(12) United States Patent
Blankevoort et al.

(10) Patent No.: US 11,504,243 B2
(45) Date of Patent: Nov. 22, 2022

(54) DEVICE AND METHOD FOR DETERMINATION OF THE MOMENT-INDUCED MOVEMENT OF A JOINT IMPLANT

(71) Applicant: ACADEMISCH MEDISCH CENTRUM, Amsterdam (NL)

(72) Inventors: Leendert Blankevoort, Amsterdam (NL); Arthur J. Kievit, Amsterdam (NL); Matthias U. Schafroth, Amsterdam (NL)

(73) Assignee: ACADEMISCH MEDISCH CENTRUM, Amsterdam (NL)

( * ) Notice: Subject to any disclaimer, the term of this patent is extended or adjusted under 35 U.S.C. 154(b) by 559 days.

(21) Appl. No.: 16/062,676

(22) PCT Filed: Dec. 15, 2016

(86) PCT No.: PCT/NL2016/050875
§ 371 (c)(1),
(2) Date: Jun. 15, 2018

(87) PCT Pub. No.: WO2017/105232
PCT Pub. Date: Jun. 22, 2017

(65) Prior Publication Data
US 2019/0000631 A1 Jan. 3, 2019

(30) Foreign Application Priority Data

Dec. 15, 2015 (NL) .................................... 1041624

(51) Int. Cl.
*A61F 2/38* (2006.01)
*A61B 5/00* (2006.01)
(Continued)

(52) U.S. Cl.
CPC .......... *A61F 2/3859* (2013.01); *A61B 5/4585* (2013.01); *A61B 5/4851* (2013.01);
(Continued)

(58) Field of Classification Search
None
See application file for complete search history.

(56) References Cited

U.S. PATENT DOCUMENTS

| 5,024,239 A | 6/1991 | Rosenstein |
| 5,167,612 A | 12/1992 | Bonutti |

(Continued)

FOREIGN PATENT DOCUMENTS

WO    WO-2016044651 A  *  3/2016  ............. A61B 5/026

*Primary Examiner* — Matthew Kremer
(74) *Attorney, Agent, or Firm* — Nixon Peabody LLP; Ronald I. Eisenstein; Nicole D. Kling

(57) ABSTRACT

The present application relates to an assembly for a joint (1, 2, 3, 4), the joint comprising a joint implant (5, 6) between a proximal segment of a limb that is proximal to the joint and a distal segment of the limb that is distal to the joint and in which the joint is configured to allow rotation of the proximal and distal segments with respect to one another about an axis that intersects a first plane, and to inhibit rotation in the second and third plane, both perpendicular to the first plane, the assembly being for subjecting the joint at predetermined angles of the joint rotation in the second and third plane to a defined bending moment to induce a load to the implant that causes a movement of the implant in relation to the bone of the proximal or distal segments.

17 Claims, 8 Drawing Sheets

(51) Int. Cl.
    *A61B 6/00*         (2006.01)
    *A61B 6/12*         (2006.01)
    *A61B 6/03*         (2006.01)
    *A61B 5/055*       (2006.01)
    *A61F 2/32*         (2006.01)

(52) U.S. Cl.
    CPC ............... *A61B 5/702* (2013.01); *A61B 6/12* (2013.01); *A61B 6/505* (2013.01); *A61B 6/52* (2013.01); *A61F 2/389* (2013.01); *A61B 5/055* (2013.01); *A61B 6/032* (2013.01); *A61F 2/32* (2013.01); *A61F 2/38* (2013.01); *A61F 2/3836* (2013.01)

(56) References Cited

U.S. PATENT DOCUMENTS

| | | |
|---|---|---|
| 2002/0115944 A1 | 8/2002 | Mendes et al. |
| 2012/0046540 A1 | 2/2012 | Branch et al. |

\* cited by examiner

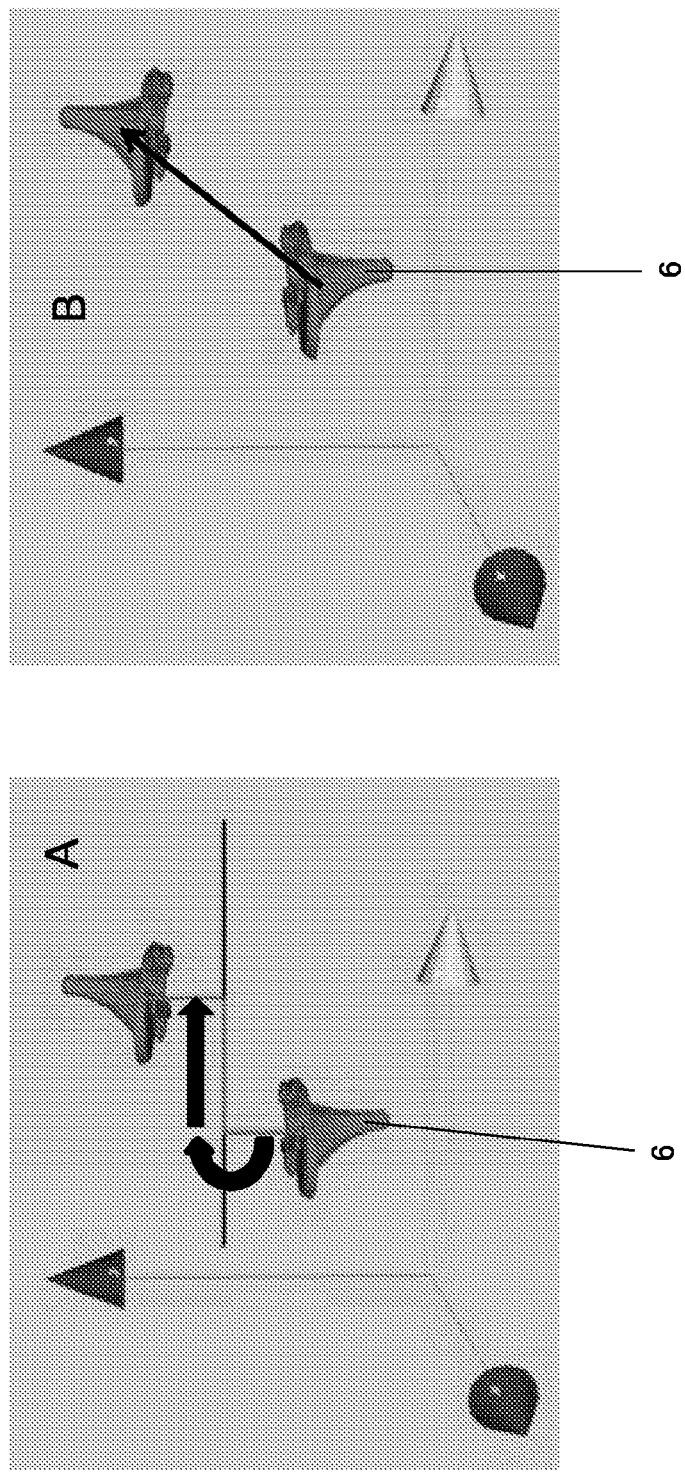

DEVICE AND METHOD FOR DETERMINATION OF THE MOMENT-INDUCED MOVEMENT OF A JOINT IMPLANT

CROSS REFERENCE TO RELATED APPLICATIONS

This application is a 371 National Phase Entry of International Patent Application No. PCT/NL2016/050875 filed on Dec. 15, 2016 which claims benefit under 35 U.S.C. § 119(b) of NL Application No. 1041624 filed Dec. 15, 2015, the contents of which are incorporated herein by reference in their entirety.

The present disclosure is related to the use of a system and method for postoperatively determining the motion of an implant relative to the bone after joint implant, and in particular, the stability of the implant or implants in the bones to which the implant is attached to, such as tibia and/or the femur after knee arthroplasty.

Joints, such as the elbow, shoulder, hip, knee and ankle, tend to be subject to wear, injury, and inflammatory diseases. Among those, osteoarthritis, rheumatoid and psoriatic arthritis, cartilage tears and defects can lead to debilitating pain, which may require a joint replacement.

In particular the human knee as the single largest joint of the human body is particularly vulnerable to damage and wear.

This joint consists principally of an upper bone, referred to as the femur, and a lower bone, referred to as the tibia, which are hinged together at the knee joint. The actual knee joint is largely constituted by femoral condyles, covered by hyaline cartilage supported in an engagement with the hyaline cartilage and crescent-shaped fibrocartilage structures, named menisci, on the tibia. The knee joint is held together by capsule, ligaments, muscles and tendons. The patella is a bone supported by the anterior aspect of the femur. The articular surfaces are covered by hyaline cartilage. The patella is connected by tendons to the tibia and quadriceps muscle and thus acts as a raiser of the lever arm of the quadriceps muscle.

When a knee joint is damaged from accident, wear, or disease, in particular as treatment for arthritis of the knee, partial or total knee joint replacement, referred to as knee joint arthroplasty, may be required. This surgical procedure is intended to replace the weight bearing surfaces of the knee joint by non-biological material to relieve pain and disability, either as partial or a total knee replacement.

Typically, the surgery comprises removal of the diseased or damaged joint surfaces of the knee, and insertion of metal and polymeric composite implants typically comprising a tibial and a femoral implant, shaped to allow continued motion of the knee. The implants are often fixed to the bone by a suitable filler, referred to herein as bone cement, composed to act as mechanical interlock with the bone and implant and/or as a filler. Other methods for fixation include gradual ingrowth of bone to the surface of the implant, which then typically is configured to offer a porous surface and/or a suitable coating, such as a hydroxyapatite coating, or any other surface that promotes bone ingrowth. The implants also comprise posts or anchors to support the fixation, which are intended to provide additional support when the joint is subjected to shear, tipping and moment loads present during normal knee function. The femoral implant typically comprises two curved convex semi-spherical shells that are connected by a curved plate, which cover the femoral condyles and typically engage the suitably shaped bearings of the tibial implant. The tibial implant is typically substantially flat and engages the tibial platform. Interaction of opposing surfaces of the femoral implant and the tibial implant allows the prosthesis to function in a manner equivalent to a natural knee joint.

Proper alignment of prosthetic components during the surgery as well as proper fixation of the implants in the period thereafter are important factors for the longevity and function of an implant. This is generally relevant for any joint or bone implant.

However, experience shows that even when properly aligned, one or more components of the implant may not be sufficiently attached to a bone initially, will remain lose or become lose over time. This may occur either because the cement loses its hold on the implant, or because the bone dissolves from around the cement or the implant, or because of an infection of the implant, or because of breakage or wearing out of the implant, or damage to the cement or to the bone surrounding the implant.

In the case of total knee arthroplasty, up to 13% of patients having been subjected to a total replacement of the operable surfaces of the knee joint required revision surgery within ten years of the surgery, as illustrated for instance by G. Labek, M. Thaler, W. Janda, M. Agreiter, and B. Stöckl, "Revision rates after total joint replacement: cumulative results from worldwide joint register datasets., J. Bone Joint Surg. Br., vol. 93, no. 3, pp. 293-7, March 2011. Loosening of one or more implant components remains one of the main reasons for these revisions, as disclosed for instance in K. J. Bozic, S. M. Kurtz, E. Lau, K. Ong, V. Chiu, T. P. Vail, H. E. Rubash, D. J. Berry, *The epidemiology of revision total knee arthroplasty in the United States*, Clin. Orthop. Relat. Res., vol. 468, no. 1, pp. 45-51, January 2010, and Patel A, Pavlou G, Mújica-Mota R E, Toms A D. The epidemiology of revision total knee and hip arthroplasty in England and Wales: a comparative analysis with projections for the United States. A study using the National Joint Registry dataset. Bone Joint J. 2015 August; 97-B(8):1076-81.

Typically, if a patient experiences persisting pain after insertion of one or more implants, especially motion dependent pain, loosening of the implant may be suspected, which in many cases is the result of aseptic loosening of one or more components of the implant.

Prosthetic loosening to date is mainly diagnosed in an indirect manner, using occurrence of pain, and by exclusion of other causes, such as infection or tumor. Currently used imaging modalities include radiography, bone scintigraphy and PET-CT. All of these methods have in common that they only deliver an indirect sign of suspected implant loosening. These modalities are currently insufficient and lead to 1 in 4 patients having a fixed implant intra-operatively when it was diagnosed as loose pre-operatively. The direct sign of mechanical loosening of the implant, i.e. the movement between bone and the implant or between bone and the cement layer is currently not evaluated in the routine clinical setting.

As a result, in an estimated 30% of all revision surgeries of a total knee arthroplasty, no implant loosening was found, due to inaccurate diagnostic techniques for mechanical loosening, as set out in the review article published by the American College of Radiology, Imaging After Total Knee Arthroplasty, ACR Appropriateness Criteria, pp. 1-16, 2011. All imaging modalities as set forth herein only give indirect clues as to the diagnosis of a loose implant component.

As revision surgery is both technically and economically demanding, optimizing a way to diagnose implant loosening would result in higher quality of care, and reduced health care cost. It can be concluded that a correct diagnosis of implant loosening requires a method to evaluate the looseness of the implant relative to the bone by an evaluation of the amount of movement of the implant component relative to the bone.

Consequently, there is a need for a system, apparatus and method to measure and analyze the amount of movement of an implanted component of a prosthesis relative to the bone, either in a joint or a bone, especially for the knee prosthesis, under conditions that cause the movement.

Yet further, since even well implanted prostheses allow for some relative movement of the prosthetic component relative to the bone as caused in part by elastic deformation of both bone and implant material, there is the need for a system and method that should, in a repeatable manner, discern between a loose implant versus an elastic movement of a well-fixed implant relative to the bone. The system should also be easy to install with respect to a patient and yet also be easily removable when the analysis is complete, and it should also allow for a high repeatability to permit an analysis of implant movement relative to the bone over time.

SUMMARY OF THE INVENTION

In a first aspect, accordingly, the present invention relates to an assembly for a joint, the joint comprising a joint implant or arthroplasty between a proximal segment of a limb, also referred to as extremity, that is proximal to the joint and a distal segment of the limb that is distal to the joint, the said assembly is attached to the proximal and distal segments and is configured to allow rotation of the proximal and distal segments with respect to one another about an axis that is perpendicular to a first plane, and to inhibit rotation in the second and third plane, both perpendicular to the first plane, the assembly being for constraining the joint at predetermined angles of the joint rotation in the second and third plane, and subject the joint to a defined bending moment in the first plane with the effect to induce a load to the components of the implant that causes a movement, also named induced movement of the implant relative to the bone of the proximal or distal segments, the assembly comprising: (a) a proximal element configured for fixation of the proximal segment; (b) a distal element configured for fixation of the distal segment; and (c) a loading assembly configured to apply a desired load exposure to the proximal and distal elements to achieve a bending moment between the proximal and distal element in the first plane of the assembly.

In a second aspect, the invention relates to a method employing the assembly defined above, the method including obtaining imaging data associated with the spatial positon and orientation of the implant in the joint relative to the bone of the first or second segment under at least two opposing load exposures, of which one can be an unloaded condition; preparing a contour image and/or a three-dimensional images of the bones and the implant components based on the imaging data under each load exposure; and analyzing the spatial data for determination of induced movement of the implant components relative to the bone.

Hence, the present invention provides a method for the determination of the movement of an implant in a knee joint, for example, using digital geometry processing. Preferably, the angle of joint flexion is in a manner that relaxes the soft tissue around the joint so not to interfere with the resulting force on the implant components in the joint. More specifically, the invention relates to a method for the determination of the moment-induced movement of a joint arthroplasty attached to a bone, in a joint between distal and proximal bones of an extremity, under a bending moment applied to the joint in a first plane defined by the direction of the moment, using digital geometry processing, the method comprising: (a) positioning the extremity comprising the joint at a predetermined angle of joint flexion of the joint motion in a manner allowing rotation of the joint about an axis that normally intersects the first plane, and inhibiting rotation of the joint in any plane perpendicular to the first plane, and (b), exerting a predetermined amount of moment on the joint in a first direction in said first plane, and, using digital geometry processing, measuring the position and orientation of the arthroplasty relative to the proximal and/or distal bones to obtain a first set of spatial location position and orientation data; and (c) exerting a predetermined amount of moment on the joint in a second direction opposing to the first direction, and, using digital geometry processing, measuring the position and orientation of the arthroplasty joint implant relative to the proximal and/or distal bone to obtain a second set of spatial location position and orientation data; and (d) comparing said measurements as described in (b) and (c) to determine a movement of the arthroplasty relative to the bone to which it is attached, where (b) can suitably be replaced by an unloaded condition and the movement is determined by comparison with the measurement as described in (c).

The term "(bending) moment (of force)" herein is the reaction induced in a structural element, i.e. a joint or bone including one or more implants, when an external force couple or moment is applied to the element causing the element to bend. A force couple is defined as two opposing forces of equal magnitude not sharing the same line of action.

The term "movement" is described by the translation and rotation between the position and orientation for a first and the position and orientation for a second load.

The term "arthroplasty" and "implant" are used exchangeable throughout this document, whereby arthroplasty refers to the surgical replacement of a joint or joint surface with an implanted prosthesis, or "implant".

According to the invention, a predetermined amount of moment may be applied to the joint, first in one direction (for instance lateral), and measuring the position of the joint implants relative to the bone using imaging techniques to obtain a set of spatial position and orientation data. Then a predetermined amount of moment is exerted on the joint in the opposite second direction (for instance medial), and the position and orientation of the joint implant relative to the bone is measured again to obtain a second set of spatial position and orientation data. The data can then advantageously be compared for position and orientation changes. Alternatively, the position and orientation can also be measured for the unloaded joint. and compared to either of the two loading condition In another preferred aspect, the method includes a system for the analysis of movability of an implant in a joint, comprising (i). an assembly according to the first aspect, ii. a suitable measurement apparatus, preferably an imaging modality, including, but not limited to CT Scanners, MRI scanners, Ultrasound, X-ray and similar devices, and iii. a computer-readable storage medium having instructions executable by at least one processing device that, when executed, causes the processing device to determine the position change of an implant in a bone.

In yet a further aspect, the present invention also relates to a method for obtaining spatial data for joint implants, to determine microscopic changes in the position and/or orientation of the implant under load relative to the bone which may indicate looseness or laxity of the joint implant.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The present invention will become more fully understood from the detailed description and the accompanying drawings, for this purpose illustrated for the knee joint, wherein.

In case of other joints, the first direction and the opposite direction rare chosen such that the bending moment allows to load the relevant implant or implants in a typical fashion that is required for measuring the looseness of the implant or implants.

Figure 3A:
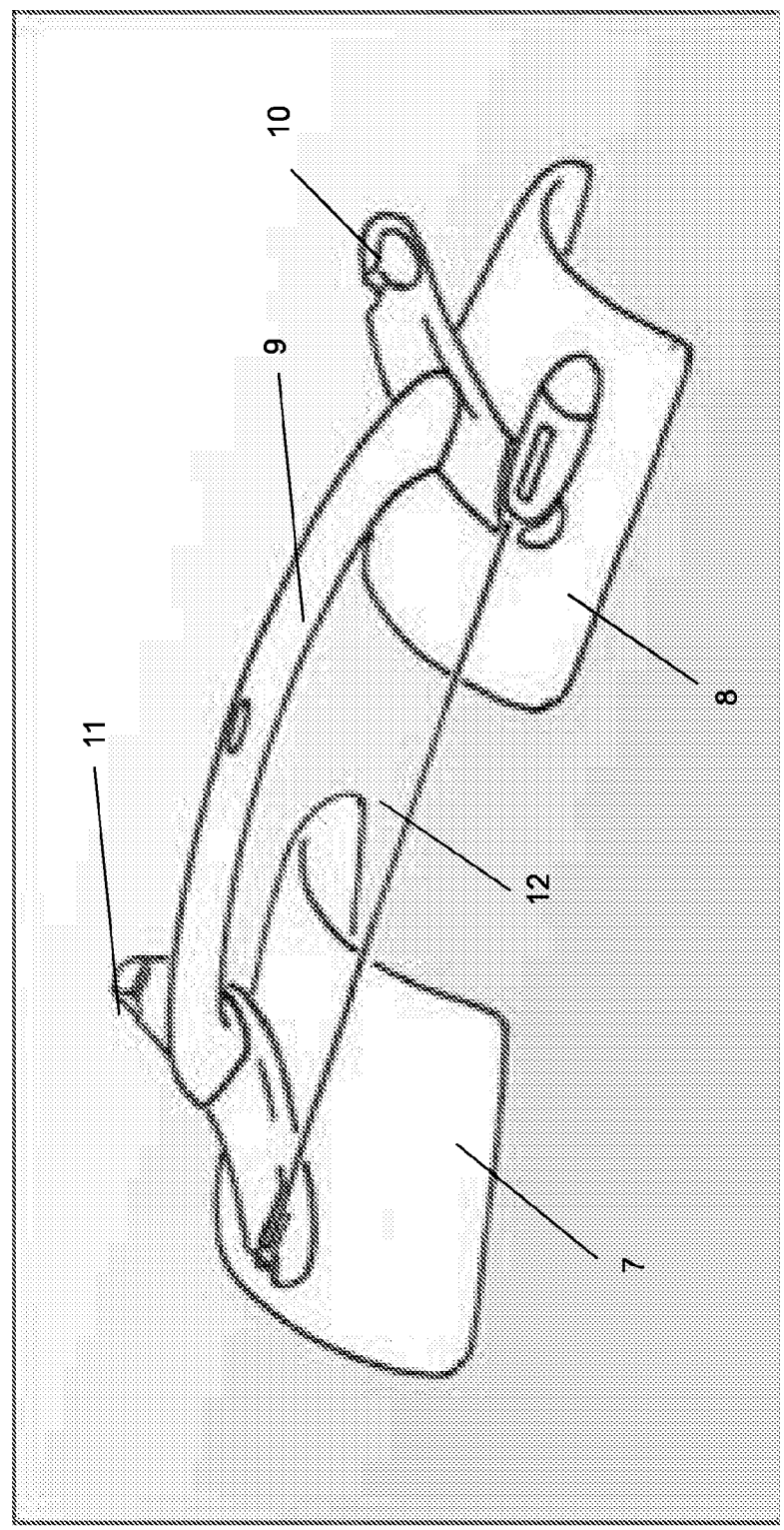
Figure 3B:
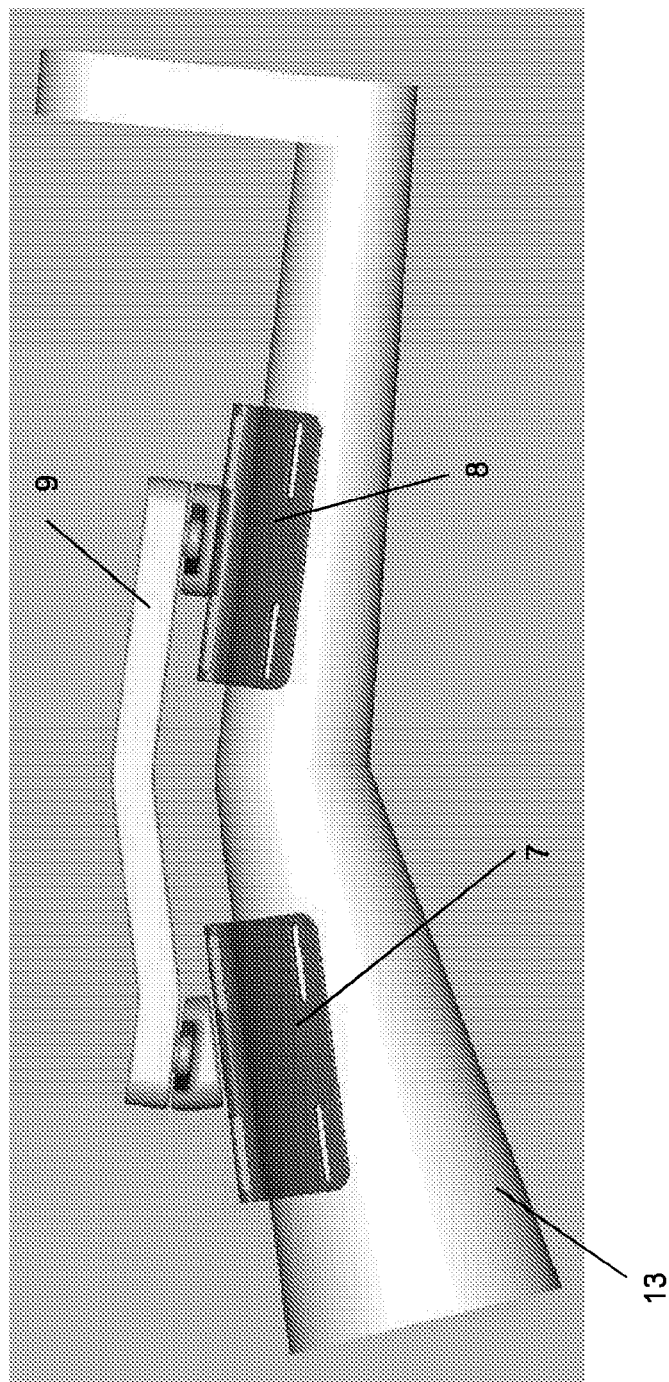

FIG. 3 illustrates a preferred method and device according to the invention: FIG. 3A shows an exemplary image of a preferred assembly according to the invention, comprising a proximal element (7) and a distal element (8) and a linking element (9), as well as arms 10 and 11 attached to the linking element and the proximal (7) an distal element (8), and a tensioning device 12 for applying a predetermined bending moment. FIG. 3B shows the schematic of a patient's leg (13) positioned in a preferred assembly according to the invention, comprising a proximal (femoral, 7) and a distal (tibial, 8) element, a linking element (9) in the side view showing the position of the elements and the predetermined flexion of the limb induced by the elements 7, 8 and 9, respectively, being secured to the femoral and tibial element, and the linking element.

FIG. 4 shows the main observed induced deviations of a tibial implant (6) under stress: A: depicts the rotation (15) about the Screw Axis (14) and the translation (16) along the Screw Axis (14) Rotation, B: depicts the displacement (17) of the center of gravity.

Figure 5:
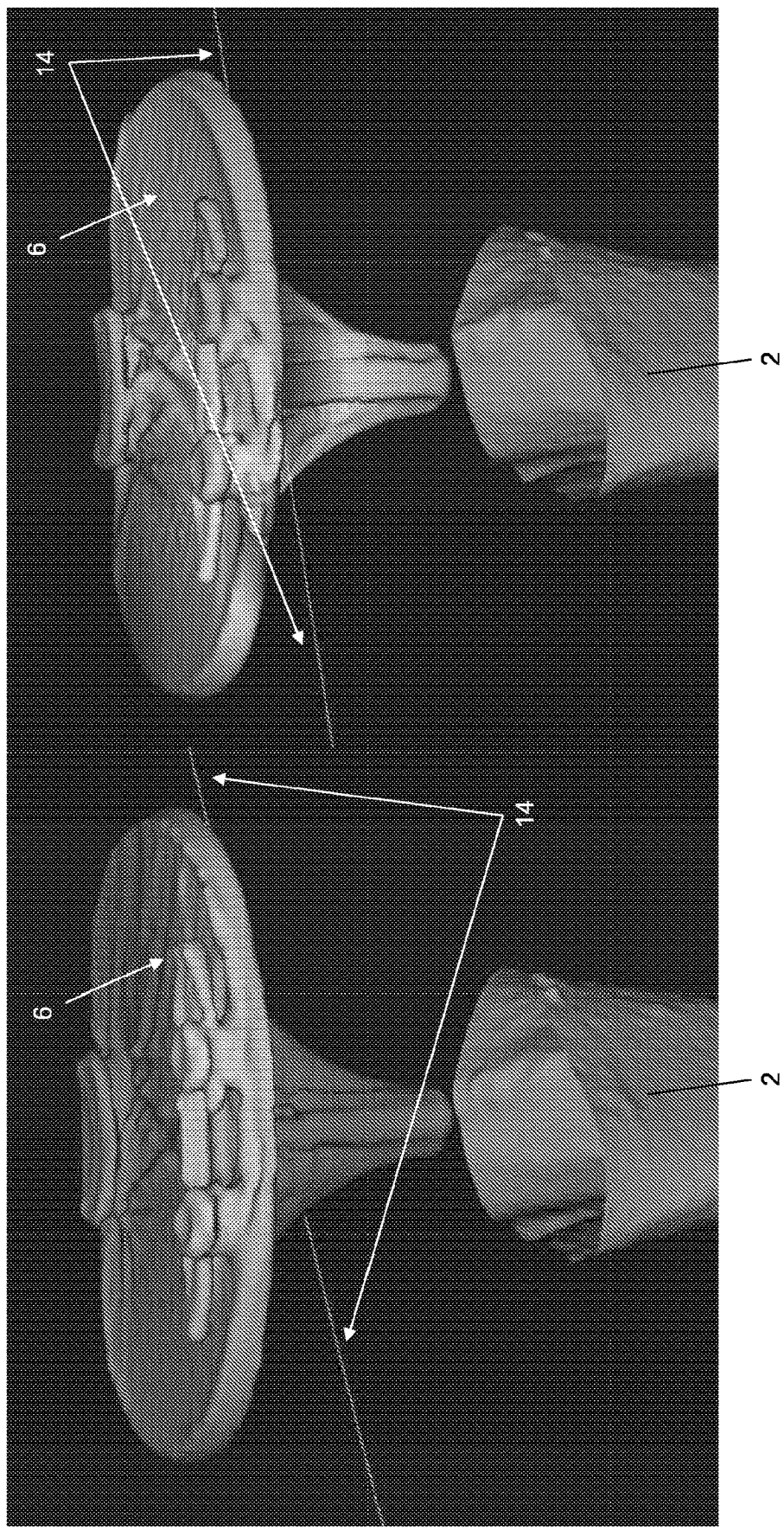

FIG. 5 depicts an actual three-dimensional image of a tibial implant. A: no observed induced movement, but elastic deformation, and B: induced movement above a chosen threshold, also visualized by the screw axis (14). The grey scales on the implant indicate the displacement of the surface points, where light grey indicates the smallest displacement and dark grey the highest displacement.

Figure 6A:
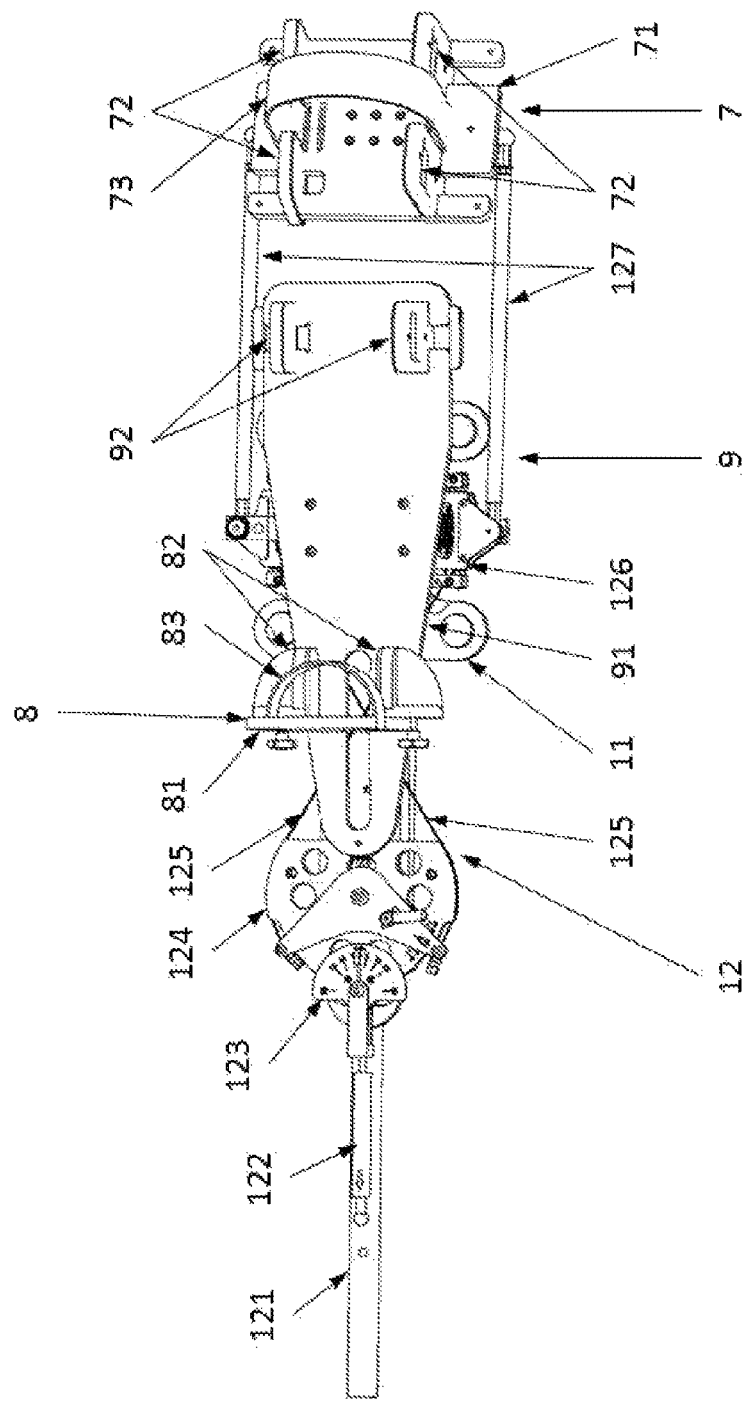

FIG. 6 illustrates a further preferred method and device according to the invention for measurement of the looseness of a knee implant. FIG. 6A shows an assembly without, and FIG. 6 B with a patient leg.

DETAILED DESCRIPTION OF THE INVENTION

As set out above, the present invention provides a method, and an assembly for the measurement of the spatial position and orientation of a joint prosthesis relative to the bone in a patient as caused by moments applied to the joint in two opposite directions, and essentially in absence of rotational freedom in the two other planes perpendicular to the plane of the moments over the knee joint that may allow for a dilation of the moment that is applied.

The invention in particular preferably relates to a combination of an assembly comprising a loading device, a method to acquire a three-dimensional image of the components of the implant and the bones, and a method to calculate the movement of each component relative to the bone that is expected to be attached to the component, whereby the loading device is used to indirectly apply a load to the joint with an implant that results in a load on the components of the implant that causes each component of the implant to move relative to the bone that it should be attached to; whereby the amount of the motion is measured from the three-dimensional scans acquired from a suitable device, such as for instance computer tomography (CT), Ultrasound, Magnetic Resonance Imaging, or any other suitable device and method; and wherein the motion is calculated from the difference in the position and orientation of the component relative to the bone between two opposite loading configurations.

The subject apparatus and method are particularly suitable for joints that comprise a proximal member, and distal member, such as, but not limited to the human knee joint, ankle, wrist joint and elbow joint. Preferably, due to the high numbers of total and partial knee replacements, the subject inventions relates to knee arthroplasty. Herein, the functional anatomic axis is defined as the line along the center of the tibial shaft about which rotation is considered to occur relative to the femur. The constraint of this rotation means that there is no rotation over his axis. Similarly the functional flexion-extension axis, defined as the axis perpendicular to the aforementioned anatomic axis in the frontal anatomic plane, is simultaneously constrained, thereby allowing only a rotation about the axis perpendicular to the anatomic and flexion-extension axis, allowing the moment applied by the apparatus to be transferred to the joint structures. The assembly preferably includes a moment mechanism configured to create a bending moment of equal magnitude at opposing sides of the joint. Thus these two bending moments both act between the proximal element and the distal element of the invention enclosing the implant in response to application of a controlled force applied over the joint, for instance in the *varus* and valgus direction in the case of total knee arthroplasty. This allows the application of a moment specifically to the joint without applying force directly onto the implant itself, but indirectly onto the implant or implants. As a result, in the case of a loose or lax implant, the load on the implant will cause an incremental induced movement relative to the bone into which the implant has been affixed by for example anchors, screws, cementation, and/or otherwise.

In the subject assembly, preferably, the proximal and distal element are configured or configurable for fixation of the respective leg segments. This may ideally be done by shaping these elements as braces, optionally comprising padding, and further comprising suitable fastening means such as straps or adjustable posts to attach firmly to the respective segments of the limb.

As set out above, the assembly further comprises a loading assembly configured to apply a desired load exposure to the proximal and distal elements to achieve a bending moment between the proximal and distal element in the first plane of the assembly; this may be done by any suitable means, e.g. springs that can be loaded, or tensioning means; preferably providing scalable, adjustable and measurable force to allow for repeatable handling by the technician involved. As preferred embodiment of a device is depicted in FIGS. 3A and B. The assembly further advantageously comprises a spacer element rotatably connecting the proximal and distal elements in the first plane or in a plane parallel to the first plane at a predetermined distance therefrom, thereby inducing the desired degree of joint flexion, while excluding movement in the planes that is not allowed, see 11 in FIGS. 3A and B for a particularly elegant solution.

The magnitude of the bending moment is the product of the magnitude of the force applied and the distance between the forces. By inversing the direction of the two opposing forces the bending moment can be reversed. The bending moment is balanced by a compression force and a distraction force or the equivalent tensile and compressive stresses in the implant and surrounding structures. The said bending moment is constant between the proximal and distal element. The implant(s) is/are thus loaded, and the forces are transmitted to achieve the bending moment.

In the case of a joint implant, the implant can carry only a compressive force. The force in the opposite direction comes from surrounding structures, such as ligaments. For a bone plate or intramedullary pin, the principle of two balancing forces does not apply with respect to the moment. Herein, a force is carried by the implant and the other by the surrounding structures. A plate or pen can withstand the total of the moment by internal pressure and tensile stresses, but will still move with respect to the bone it is fastened to.

The subject assembly, system and method may also suitably be employed for the determination of the induced movement of a bone implant, e.g. in a broken bone. In this case, the joint is referred to herein is the point where the two or more bone elements are joined together; e.g. by implants comprising a pin, nail, plate, rod and/or screw, such as for instance intramedullary nails, rod or pins used for instance in femoral fractures, such as supracondylar femoral fractures, or intra distal femoral intramedullary attachments. As in rotating joints, e.g. knee or elbow joints, these intramedullary joints may show a moment induced movement over time, and my cause pain and instability in the bone thus treated if the implant is loose, or at least if not firmly attached. The present invention also relates to a method to determine the moment induced movement over a joint connecting a fractured bone comprising an implant, preferably after allowing bone and implant to heal for a suitable period of time. In such a joint, the predetermined degree of flexion is quite low, in line with the normal geometry of the bone.

The moment may be applied by any suitable means. In a preferred embodiment, a force applying device is employed having a surface to engage the joint laterally from lateral directions that allow for the determination of the induced movement. In the example of the total knee arthroplasty, this would be in coronal plane in the *varus* and the valgus direction, respectively, thereby resulting in the moment being transferred onto the joint. In the case of a partial knee arthroplasty, thus a unicompartimental replacement, the direction may advantageously be in the sagittal plane, i.e. applied from the ventral and dorsal direction.

Accordingly, for a unicompartimental replacement, the present invention relates to a method and a system for the determination of the moment induced movement of a total or partial joint implant attached to a bone, in a joint between distal and proximal bones of an extremity, under a bending moment applied to the joint in a first plane defined by the direction of the moment, the method comprising: (a) positioning the extremity at a predetermined angle of joint motion in a manner allowing rotation of the joint about an axis that intersects the first plane, and inhibiting rotation of the joint in any plane perpendicular to the first plane, and in such fashion that the extremity is not subject to any external load and, using digital geometry processing, measuring the position and orientation of the arthroplasty relative to the proximal and/or distal bones to obtain a first set of spatial position and orientation data; (b) exerting a predetermined amount of moment on the joint in a first direction in said first plane, and, using digital geometry processing, measuring the position and orientation of the arthroplasty relative to the proximal and/or distal bones to obtain a second set of spatial position and orientation data; and (c) comparing said measurements as described in (a) and (b) to determine a movement of the joint implant relative to the bone to which it is attached. Preferably, the method also comprises positioning the extremity at a predetermined angle of joint motion in a manner allowing rotation of the joint about an axis that intersects the first plane, and inhibiting rotation of the joint in any plane perpendicular to the first plane, and, using digital geometry processing, measuring the position and orientation of the arthroplasty relative to the proximal and/or distal bones to obtain a first set of spatial position and orientation data; (b) exerting a predetermined amount of moment on the joint in a first direction in said first plane, and, using digital geometry processing, measuring the position and orientation of the arthroplasty relative to the proximal and/or distal bones to obtain a second set of spatial position and orientation data; and (c) comparing said measurements as described in (a) and (b) to determine a movement of the joint implant relative to the bone to which it is attached.

This means that the data for the partial knee joint may advantageously be collated by comparing a leg at a given flexion, and a leg that is overstretched in the sagittal plane.

This method may advantageously not only be employed for partial, but also for total joint prosthesis, or any other kind of implant, provided a sufficiently measurable movement of the implant vis-à-vis the bone or bones can be induced. Herein, the position of an implant is measured in a force loaded, and an unloaded position, and compared with respect to the position of the implant versus the bone.

Generally, in the subject assembly and method, application of pressure or tensile force of equal amounts is done over a joint, in which the forces are parallel to each other and do not coincide. The bending moment induced over the joint is then equal to the product of the force and the distance between the two forces.

The subject assembly differs from known assemblies, such as the orthosis disclosed in U.S. Pat. No. 5,167,612 A, or the apparatus disclosed in US 2012/046540 A1 in at least a number of the following features.

U.S. Pat. No. 5,167,612 discloses an adjustable orthosis for stretching tissue by moving a joint between first and second relatively rotating body portions includes a first arm with a cuff at its outer end for releasably attaching the first arm to the first body portion, and a second arm with a cuff at its outer end for releasably attaching the second arm to the second body portion. The arms are pivotally connected at their inner ends. In this orthosis, the proximal and distal elements of the disclosed device pivot with the illustrated elbow. Contrary to this orthosis, and its method, the present assembly maintains a defined given degree of flexion in the joint, while the proximal and distal elements of the assembly twist relative to one another to pivot the device and the attached leg bones normal to a knee in a *varus* and valgus direction, with a specific moment, and at the given degree of flexion. This is not feasible with the disclosed orthosis, at least not without significant modifications, none of which are suggested in U.S. Pat. No. 5,167,612 A.

US 2012/046540 A1 describes a system that requires three connected bones. A proximal bone, such as a femur is fixed by fixing the upper thigh in a holder; a distal bone, i.e. the foot is rotatably, i.e. revolvingly or rotatingly affixed as well, and an intermediate bone, i.e. the tibia, is free to rotate with the distal bone around the ankle. This however does not show an induced effect on the actual implant, but only the flexibility and rotation capability of the entire knee, and not a force inducible displacement of the implant versus the bone.

The subject assembly provides the application of a tensile force and a compression force to a joint, whereby the compressive and tensile force are of equal magnitude, are parallel to each other and do not coincide. The moment thus obtained is then equal to the product of the force and the distance between the two forces, and is referred to herein as the "bending moment" over the joint. The direction of bending or rotation of the proximal and distal elements of the assembly thus twist relative to one another; and thereby apply the bending moment over the joint in a direction that is not the normal bending direction of the joint, but is perpendicular to it.

The proximal and distal elements of the subject assembly are adapted to be mounted on a member adjacent to, and on opposite sides of, a joint, e.g. the upper and lower thigh in the case of a knee joint; or the upper and lower arm in case of an elbow.

In a preferred embodiment, the moment is applied by tensioning the proximal and the distal element through a suitable tensioning device, thereby delivering the moment to the joint, while maintaining the extremities in position to not allow bending of the joint in response to the forces applied.

Without wishing to be bound to any particular theory, it is believed that when a prosthesis or implant is not affixed appropriately in a bone, more movement and rotation is possible than when it is appropriately fixed to the bone, beyond the flexibility inherent to bone, cement and prosthesis.

To determine the induced movement of an implant in a joint, spatial translations and rotations are employed to describe six degrees of freedom of motion of a rigid body in a Cartesian coordinate system. A change in position and orientation, also referred to as total displacement, can advantageously be described by a translation vector in combination with a rotation matrix. First a decision on the position of the origin and direction of three axes of the coordinate system is made. These axes are all perpendicular to each other and usually defined as X, Y and Z. In relative motions one of the bodies of movement is considered stationary. The translations along the axes of the Cartesian system originate from the translation vector. The component rotations about the axes of the coordinate system can be derived from the rotation matrix and depend on the order of rotation, as well as the choice for the stationary (reference) body.

Any suitable parameter derived from the aforementioned translations and rotations or rotation matrix may be employed within the method of the present invention for determination of the induced movement that is indicative of a loose implant, such as screw axis rotation, and total displacement.

Within the present specification, the term "screw axis" refers to the Helical Axis of Motion (HAM), which is a line around which an object rotates and over which it translates, thus a line that is simultaneously the axis of rotation and the line along which the translation occurs. It is used herein to denote the induced translation of the implant. Generally, the screw axis is a representation of the change of position and orientation of a rigid body. It can be determined from the translation vector in combination with the rotation matrix (see FIG. 6A).

By using the screw axis, every change in position can be described in six degrees of freedom as long as the position and orientation of the axis and the translation over, as well as the rotation around the axis are known. It consists of the unit vector (n) of the axis itself, the rotation phi ((p) and translation (t) of the rigid body, and a radius vector (s) which describes the position of the axis relative to the rigid body. The calculation of helical axis parameters from the rotation matrix R and the translation vector a is preferably performed as follows:

Given the rotation matrix R and translation vector a, describing the motion of a rigid body, the position of a point p on that body changes according to formula I:

$$p_t = R \cdot p + a \qquad \text{I}$$

wherein $p_t$ is the position of p after the translation and rotation of the body.

The helical axis describing the very same motion may be represented by a rotation about and a translation along an axis in space. From R and a, the corresponding helical axis parameters are calculated according to formula II:

$$\varphi = a\sin(0.5 * \sqrt{((R(3,2)-R(2,3))^2 + (R(1,3)-R(3,1))^2 + (R(2,1)-R(1,2))2))} \qquad \text{II}$$

and formula III:

$$n = [R(3,2)-R(2,3), R(1,3)-R(3,1), R(2,1)-R(1,2)]/2 \sin \varphi, \qquad \text{III}$$

wherein φ is the rotation about the helical axis and n is the unit direction vector of the helical axis.

The translation v along the helical axis is calculated from formula IV $$v = n \cdot a \qquad \text{IV}$$

The position s of a point on the helical axis is calculated from formula V $$s = (\sin(\varphi)/(2(1-\cos(\varphi)))) (n \times a) \times (n \times (n \times a))/2 \qquad \text{V}$$

Note that R(i,j), for i=1, 2, 3 and j=1, 2, 3, denotes the components of matrix R.

In the above formulae, x represents the cross product of two vectors and • represents the dot product of two vectors.

This is disclosed also in FIG. 3A, wherein an illustration of the screw axis of a tibial implant is given. Here the black line represents the axis, the black arrow the rotation over the axis and the dark gray line the translation.

FIGS. 6 and 6A illustrate a preferred embodiment of an assembly according to the invention. Herein, the following table 1 shows a legend for the terms and the corresponding reference numbers:

TABLE 1

Reference numbers for FIGS. 6A and B.

| Ref. No. | Part | Function |
|---|---|---|
| 7 | Thigh fixation unit | Fixation of the thigh |
| 8 | Foot fixation unit | Fixation of the foot |
| 9 | Shank fixation unit | Fixation of the shank |
| 11 | Movable support plate | Allows free motion in the support plane |
| 12 | Load application unit | Generates a force couple between 7 and 8&9 |
| 13 | upper leg | |
| 14 | lower leg | |
| 71 | Thigh support plate | Supports the thigh |
| 72 | Thigh fixation posts | Fixates the thigh |
| 73 | Thigh fixation strap | Additional thigh fixation |
| 81 | Foot plate | Holds the foot |
| 82 | Ankle fixation posts | Fixates the ankle |
| 83 | Foot fixation strap | Fixates the forefoot |
| 91 | Shank support plate | Supports the shank |
| 92 | Shank fixation posts | Fixates the shank, with 82 & 83 fixates the lower leg |
| 121 | Handle bar | Operates the load application unit (12); moving the handle bar will change the moment arm of the force (122) |
| 122 | Constant force unit | Unit that provides a constant force |
| 123 | Moment dial | A dial of the moment reading |
| 124 | Force plate | Conveys the force to the force cable (125) |
| 125 | Force cable | Conveys the force to the differential unit (126) |
| 126 | Differential unit | Transforms the force to a couple forces of equal magnitude and opposite direction to the force bars (127) |
| 127 | Tensile & compressive force bars | The couple forces results in a bending moment between 7 and 8 & 9. |

Figure 6B:
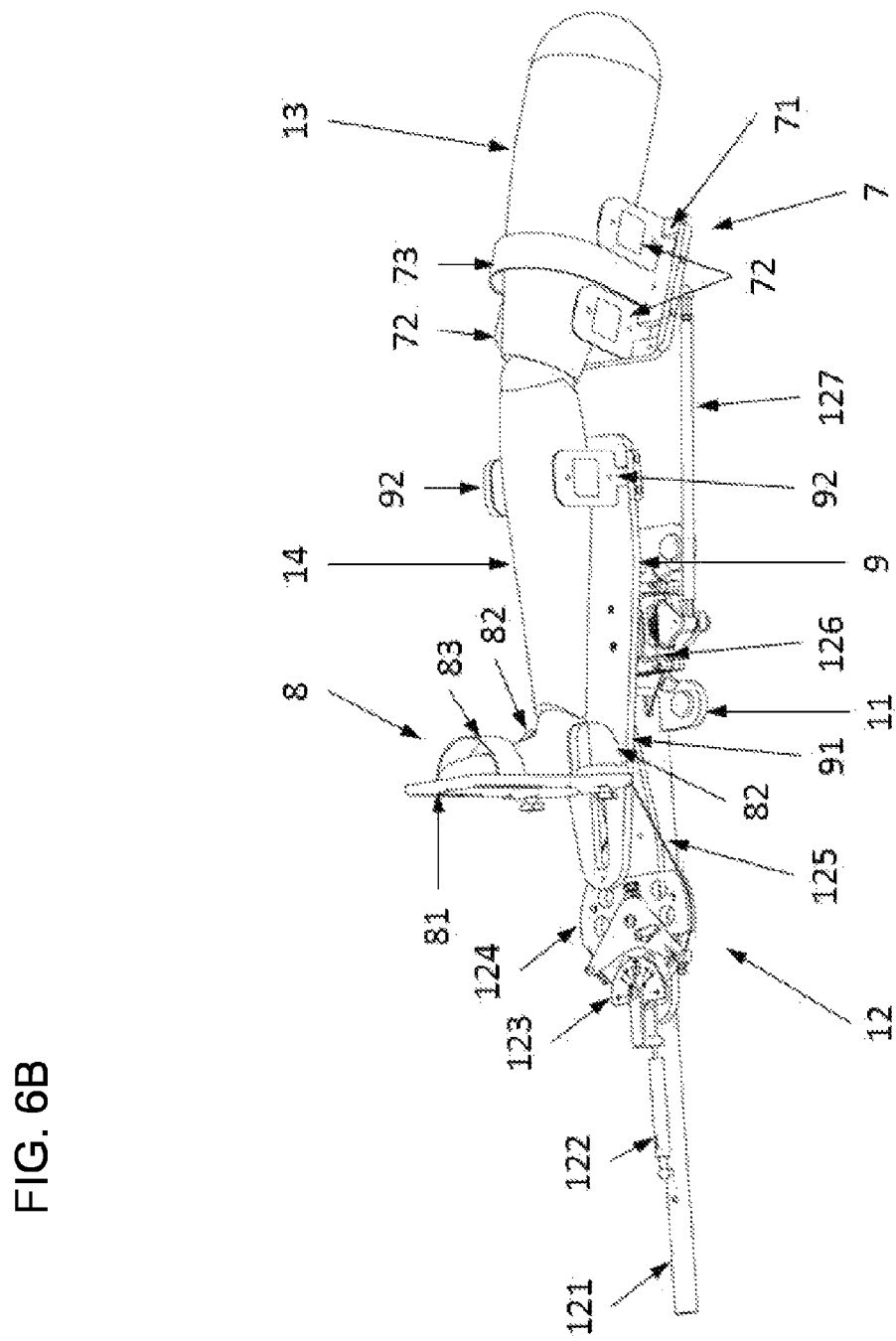

As illustrated in FIG. 6B, when a patient's leg is positioned in the assembly according to FIG. 6A, by moving the handle in either way, a technician may put identical yet opposite forces on either side of the knee from the *varus* and *vagus* direction, respectively. The assembly allows high repeatability, and excludes operator variation, thereby rendering the operation highly repeatable.

The assembly is preferably essentially made of low density materials, such as polymeric materials. Metals, such as aluminum or steel, are only employed where required, e.g. for force springs.

The present invention also relates to a method for the determination of the induced movement of a prosthetic bone implant in a joint using digital geometry processing, comprising (a) positioning the limb comprising the joint at a predetermined angle of flexion in a manner that does essentially not allow rotation of the joint over a proximal and/or distal central axis to dilate a moment exerted on the joint, and exerting a predetermined amount of moment over the joint in a first lateral direction, and measuring the position of the joint implants relative to the bone to obtain a first set of spatial position and orientation data; and (b) exerting a predetermined amount of moment on the joint in a second lateral direction essentially opposite to the first direction, and measuring the position of the joint implant relative to the bone to obtain a second set of spatial position and orientation data, preferably whereby the joint is placed in essentially the same position for the measurement.

Preferably, measuring of the spatial position and orientation data comprises generating series of two-dimensional radiographic images taken around a single axis of. This is most preferably performed as a CT scan, employing a suitable CT scanner, but can also be performed using other suitable measurement and imaging methods, including but not limited to ultrasound, Röntgen/X-ray, MRI, bone scintigraphy or (S)PE(C)T-CT.

While Röntgen-or X-ray stereometric analysis under induced movement has been used for several years, generally this method was found quite cumbersome, as it requires the presence of markers in the implant and/or affixed to a bone, and/or an exact description of the geometry of the implant. Also it was found that the a small change of the position and orientation of the implant relative to the bone was difficult if not impossible to measure by conventional Röntgen/X-ray methods. The present method advantageously allows to achieve high accuracy, and does not require the presence of markers, or knowledge of the exact geometry of the implant.

The method further preferably further comprises (c) calculating a positional and orientational relationship between at least one of the implants and the patient's proximal and/or distal bone based on spatial position and orientation data.

Advantageously, step (c) comprises step (d) of generating contour images of the implant or implants relative to the bone from the data obtained in steps (a) and (b). Digital geometry processing is preferably used to generate a contours and/or three-dimensional images of the joint implant and bones from the series of two-dimensional radiographic images taken along a single axis.

The method further preferably comprises step (e) of superimposing the contour of the three-dimensional digital models to identify and determine a variation of the induced translation and angulation of the implant with respect to the bone, i.e. the relational spatial position and orientation, a preferred embodiment of which is disclosed herein below.

Advantageously, the method further comprises comparing the induced movement with a threshold value, and determining whether the movement is above the threshold value, indicating a laxity of the implant in the respective bone. The term "movement" herein refers to the induced movement of the implant, such as the translation along a screw axis, rotation about the screw axis or the total displacement.

The term "laxity" refers to the looseness of the implant in the bone. Accordingly, the present invention also preferably relates to the method, wherein measuring of the spatial position and orientation data comprises generating a series of two-dimensional radiographic images taken along a single axis, preferably as CT or MRI scan. More preferably, the method further comprises step (e) of calculating a positional and orientational relationship between at least one component of the implant and the proximal or distal bone segments in the proximal and distal segments of the limb based on the spatial position and orientation data. Advantageously, step (d) comprises a step of generating contour images of the joint implant, and contour images of the proximal and/or distal bones from the data obtained in steps (b) and (c). Preferably, digital geometry processing is used to generate contour images of the joint implant orientations and positions and the bone orientations and positions from the series of two-dimensional radiographic images taken along the single axis. The method may preferably further comprising the step of superimposing the contour images to generate three dimensional images, and/or to identify and determine a variation of the angulation, total displacement, and/or screw axis of the arthroplasty with respect to the bone to which it is attached.

More preferably, the method further comprises comparing the variation of angulation, total displacement, and/or screw axis with a threshold value, and determining whether the angulation, total displacement or screw axis parameters are above the threshold values. In a preferred embodiment, the joint is a knee joint, and the threshold for the screw axis is in the range of from 1.0° to 1.5° at an applied moment of 20 Nm.

In a further preferred embodiment of the method, the images are time-resolved images for generating data output of inducible movement of the implant over time, thereby allowing monitoring of progression of inducible movement of the implant or implants over time, and disease or change associated with a therapy, or allowing visualizations and associated calculated measurements associated with changes in the joint structure between images taken at different time intervals. Preferably, patient images are time-resolved images for generating data output of the moment induced movement of the implant over time, thereby allowing monitoring of progression of a disease, change associated with a therapy, or allowing visualizations and associated calculated measurements associated with changes in the joint structure between images taken at different time intervals.

The present invention also relates to a system for the determination of induced movement of a joint implant under a bending moment using digital geometry processing, the system comprising: (a) an assembly as set out above, and (b) an apparatus configured and equipped for generating two-dimensional radiographic images taken along a single axis, preferably a CT- or MR scan.

Preferably, the system further comprises an element configured to position the extremity at a predetermined angle of flexion of the joint in a manner allowing rotation of the joint about an axis that intersects the first plane, and inhibiting rotation of the joint in any plane perpendicular to the first plane; a first element exerting a predetermined amount of moment on the joint in a first direction in said first plane, and a second element exerting a predetermined amount of moment on the joint in a second direction opposing the first direction in said first plane, using digital geometry processing, measuring the position of the arthroplasty relative to the proximal and/or distal bone to obtain a second set of spatial position and orientation data; and a digital geometry processing element configured for, and operable for measuring the position and orientation of the implant relative to the proximal and/or distal bones to obtain a first set and a second of spatial position and orientation data; and a data processing device configured for, and operable for comparing said spatial position and orientation data to determine a movement of the implant relative to the bone to which it is attached. In a further preferred embodiment, the system further comprises a computer-readable storage medium having instructions executable by at least one processing device that, when executed, cause the processing device to determine an induced movement stability of the joint implant in relation to the bone.

Yet further, the system may advantageously further comprise a position calculation element configured for calculating a positional relationship between at least one of the implants and the proximal and distal bones in the proximal and distal extremity based on the spatial position and orientation data; the latter element for position calculation preferably configured to generating contour images of the joint implant relative to the proximal and/or distal bones from the first and second spatial data sets. A digital geometry processing element is preferably used to generate contour images of the joint implant positions from the series of two-dimensional radiographic images taken along the single axis. The present invention also relates to a system for the determination of the induced movement of a prosthetic bone implant in a joint in a limb, the system comprising: (i) an assembly as set out above, and (ii) a suitable measurement apparatus, preferably a CT Scanner, and (iii) a computer-readable storage medium having instructions executable by at least one processing device that, when executed, cause the processing device to determine the laxity of an implant in a bone.

The present invention also relates to the use of an assembly according to the invention for the preparation of 3-dimensional images of a joint implant under induced bending moment, preferably wherein de relative position of the implant versus the bone or bones is determined.

The present invention also relates to a kit of parts comprising an assembly according to the invention, an apparatus configured and equipped for generating two-dimensional radiographic images taken along a single axis, preferably a CT or MRI, and a data processing device configured for, and operable for comparing said spatial position and orientation data to determine a movement of the one or more implants to the bone to which it is attached.

The present teachings, however, are not limited to this procedure, but can be used for a number of different joint implants, including hip joint, shoulder joint, elbow joint, ankle joint, wrist joint and the like, and fracture fixation systems.

The following, non-limiting examples illustrate the invention further:

Example 1, Experiments 1 and 2

Experiment 1:
On a human leg specimen with a total knee arthroplasty, two diagnostic CT scans were made for assessing implant laxity (FIG. 4A). The first CT scan was made while a moment is applied to the distal part of the tibia in the medial direction (*varus* scan). During the second CT scan the same load is applied but in the lateral direction (valgus scan). In case of implant laxity, the position and orientation of the implant, relative to the tibia, will change between the two scans. Intensity-based point-to-image registration is used for registration of the implant and the tibia to the valgus scan. To this end, points were selected by sampling the gray-level CT image 0.3-mm towards the inside (bright voxels) and outside (dark voxels) of the segmented bone. This resulted in a double-contour polygon, which included the gray-levels at each vertex. Registration of these many gray-level points with the gray-valued valgus image rendered registration accurate. Registration results in a transformation matrix, MT, which brings the tibia polygon to the valgus image (FIG. 4A) and a second transformation matrix, MI, which aligned the implant polygon with the valgus image. These matrices could be combined to find a laxity matrix, ML, which brings the virtual implant from the *varus* to the valgus position, within the frame of reference of the *varus* scan.

In case of laxity, the implant position and orientation with respect to the tibia was found as different for the *varus* and valgus images. Laxity could be established if the change of orientation and/or position of the implant was above a given threshold. Alternatively, to quantify the induced movement, the mean target registration error (mTRE) may be employed. This parameter represents the mean distance between corresponding points of the virtual implant polygon in the *varus* and valgus positions.

The tibial implant and the tibia were segmented using the *varus* scan. Each object was first segmented using threshold-connected region growing. For the implant a high threshold (2900 Hounsfield Units (HU)) was selected to mask metal artifacts as much as possible. For bone segmentation the threshold is lower. Residual holes inside a segmented object and at the surface were subsequently filled by a binary closing algorithm.

This intermediate segmentation result was used to initialize a Laplacian level-set segmentation growth algorithm, which adjusts the edges towards the highest intensity gradient of the bone image. A polygon was finally extracted at the zero level using the marching cubes algorithm.

Figure 1:
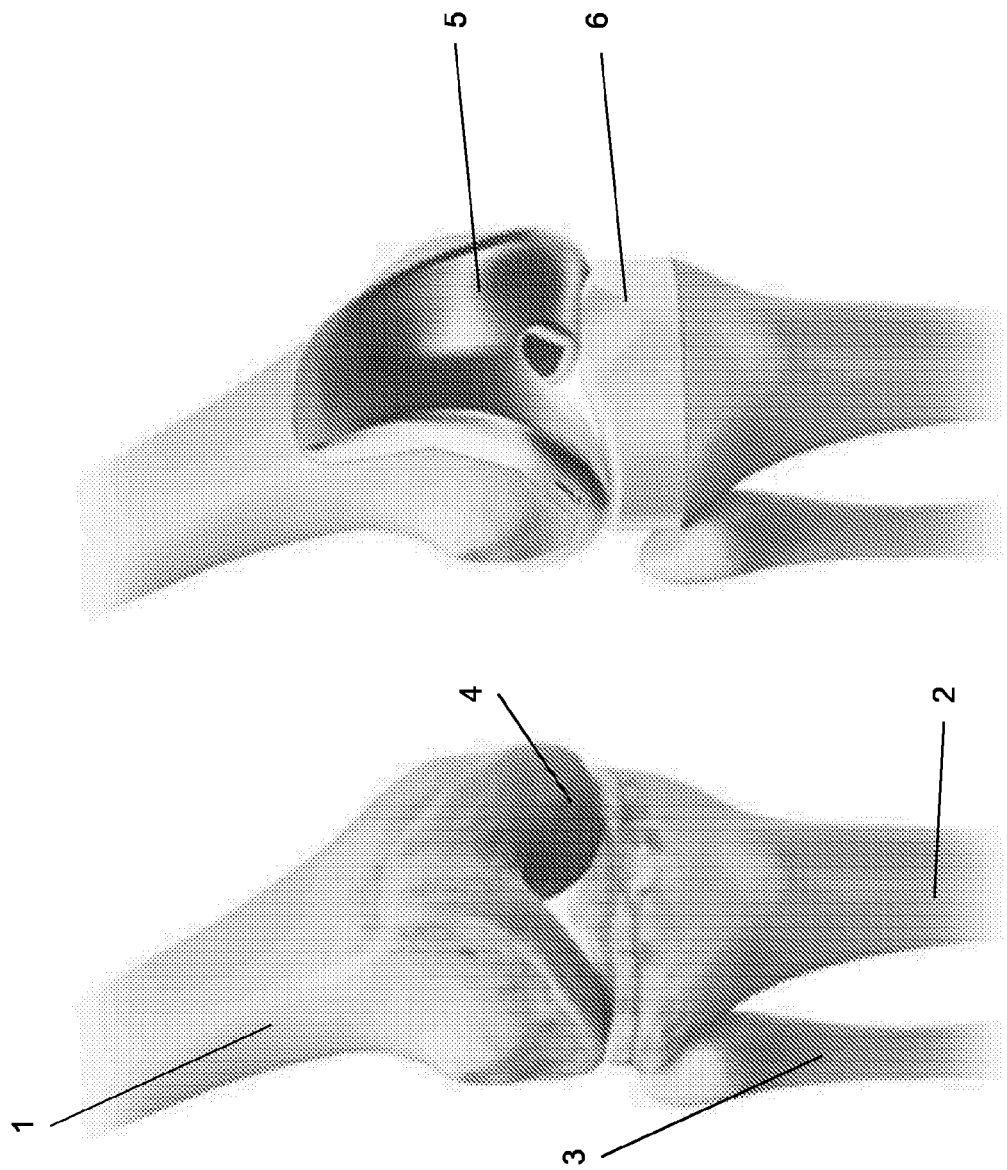
FIG. 1 is a depiction of a knee joint comprising a femur (1), tibia (2) and fibula (3), with knee joint surfaces (4), and a knee joint with a total knee arthroplasty, showing femoral (5) and tibial (6) implant components.
Figure 2:
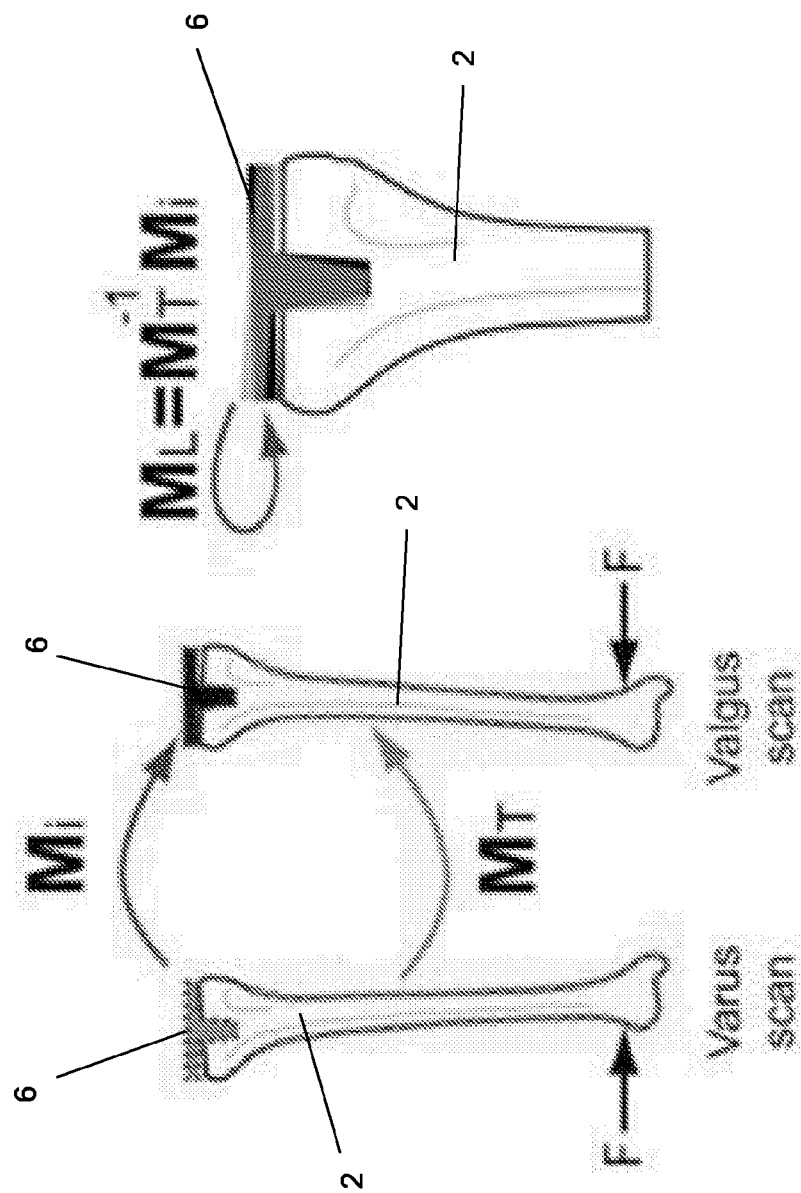
FIG. 2 illustrates the method for establishing the moment induced movement of a tibial implant (6): a) Two diagnostic CT scans are made with the tibia (2) under mechanical load (indicated by force F), that forces the tibia in to rotate in the first plane, in varus and valgus orientation. The varus image is used to segment the implant (light grey) and the tibia (dark grey). The virtual tibia and implant objects are registered to the valgus image resulting in transformation matrix $M_T$ and $M_I$ that align the tibia and implant with the valgus image. b) The matrices are combined into the laxity matrix ML that repositions the virtual implant from the *varus* to the valgus position relative to the tibia within the *varus* image.

The tibial implant caused metal artifacts in the reconstruction of the CT image. This hampered segmentation of the first proximal segment of the tibia, which, for this reason is removed by polygon clipping (FIG. 1a, dotted blue tibia segment). The resulting polygons were then used for 3-D visualization of the implant and the tibia, and for subsequent registration of both virtual objects with the same objects in the valgus scan.

The segmentation, registration and calculation in the following examples was performed using the Insight ToolKit (ITK 3.6.0, Kitware, Inc., Clifton Park, N.Y.); the visualisation was achieved by the Visualization ToolKit (VTK 5.0.4, Kitware, Inc., Clifton Park, N.Y.) and the Graphic User Interface was programmed with QT 4.3.3 (Nokia, Oslo, Norway). Segmentation results in a double-contour 3D-polygon, wherein in the registration the tibia and tibial component polygons are first separated and then matched to a background image where they are fitted in the best way possible, giving a correlation coefficient that indicates the goodness of fit. Finally, in the calculation, the translations and rotations in the x, y and z-plane are deducted from the registration step. The change in position of the tibial component compared to the change of position of the tibia is registered. From these translations and rotations the screw axis can be calculated.

Experiment 2:

This experiment involved inserting plastic spacers of various thickness between the tibial platforms and the implant, to create an artificial yet quantifiable angulation of the implant, to correlate a known distance to the spacer thickness, and displacement of the implant versus the tibia. Three wedges with increments of 0.5 mm resulted in measured displacement increments of 0.50 mm, 0.55 mm and 0.42 mm. The difference between the measured displacement and the thickness of plastic inserts used to simulate laxity was due to surface irregularities. The relative steps were accurate from the first insert onward (0.5 mm, 1.05 mm and 1.74 mm).

Error of Measurement Experiment:

to establish the measurement error of the analysis method as caused by the scanning and subsequent calculations, a single hard frozen leg was scanned in slightly different positions and orientation in the scanner for 10 consecutive times. As the leg was frozen solid no relative displacement or rotational changes should occur between the implant and the bone. The distance that is measured is therefore the measurement error of the method.

Threshold for Laxity Assessment:

Laxity causes repositioning, or movement of the tibial implant under different loads, as illustrated by Experiment 2 below. "Movement" of the implant may advantageously be expressed and quantified by rotations and translations. The accuracy and reproducibility of position measurements the way described above, depends on the noise content of the CT images, and on the Nelder-Mead downhill simplex optimization algorithm used for registration, which may result in slightly different position estimations, hence mTRE values, due to differences in manual initialization of the calculation process.

Assembly for four-point bending test of a Knee Joint Arthroplasty:

An exemplary assembly for applying a bending moment over a joint comprises a femoral and tibial element shaped as a suitably shaped brace, optionally with padding, with fastening means such as straps for the segments of the limb, and a force applicator providing a predetermined moment either in the *varus* or valgus direction (see for instance FIG. 3). Herein, a bar (9) is connect by two hinges to the tibial (8) and femoral (7) elements. The axes of these hinges are perpendicular to the *varus*-valgus plane. A load applicator in the shape of a tensioning device applied a force onto the tibial and femoral element. The knee is in flexion of 20 degrees, so as to relief tension of the collateral tissues. With respect to the assembly shown in FIG. 3, the load applicator shown here applies the force on the tibial and femoral element. This force and the counter reaction force in the bar (9) form a couple of forces that results in a moment applied to the joint between the tibial and femoral segment. To avoid rotation of the leg externally or internally when a *varus* or valgus force was applied with the leg in slight flexion, the foot may be fixed in a 90-degree angle in which rotation of the limb is not permitted, but *varus*-valgus movement still possible.

In this assembly, however, the avoidance of the rotation was achieved by the restraint of the rotation between the distal (8) and proximal (7) element. In the assembly in FIG. 3, this is achieved by the restraint of this rotation between he distal (8) and proximal (7) element.

It was found that the disclosed prototypes, which were set out as shown in FIGS. 3 and 6, did not produce unsuitable radiological scattering due to the small diameter, the use of low-density materials and small size of the parts made from dense materials.

In the device shown in FIG. 3, the femoral and tibial element each comprise a shell attached with straps to tibia and femur, respectively that convey the moment to the shank and the thigh. The device further comprised a stabilizing frame and a force application device with force measurement sensor. In the device as shown in FIG. 6 the femoral and tibial element each comprise fixation posts and straps to convey the moment to the shank and thigh. The moment dial on the load application unit indicates the moment level that is applied.

Both devices allow the application of a constant moment over the area in which the prosthesis sits between the distal (8) and proximal (7) fixation elements, thereby ensuring that no other loads are applied to the knee for the purpose of reproducibility of the load on the prosthesis and ease of positioning the device. For field practice, an assembly according to FIGS. 3A and B may suffice, however.

Quantifying the reproducibility of position measurement yielded a threshold for laxity establishment. To this end a cadaver leg was scanned, once under *varus* and 10 times under valgus load. The latter 10 scans were made under exactly the same conditions, although the noise content of the CT images was different. The *varus* scan served to segment the implant and tibia and allowed registration to all 10 valgus images. This resulted in 10 values of the mTRE. The mean (m) was used to represent accuracy and the standard deviation (SD) serves to represent reproducibility. The threshold for laxity, i.e. induced movement of the implant beyond the elasticity and product related movement expected assessment was set to m+5×SD, hereby accepting misjudging laxity in theoretically 1:872,139 cases. The accuracy and reproducibility of position and orientation measurements the way described above, depends on the noise content of the CT images, and on the Nelder-Mead downhill simplex optimization algorithm used for registration, which may result in slightly different position and orientation estimations, hence mTRE values, due to differences in manual initialization. Quantifying the reproducibility of position measurement yields a threshold for laxity establishment.

Example 2

Following Example 1, a larger study involving 10 leg specimens was devised. At first a situation representing loose implants was simulated. Following bone preparation a cemented implant was inserted without cement. After implantation, each implant was manually moved around slightly to simulate an area of bone resorption as found around loose implants, to ensure the prosthesis was no longer press fit, as laxity of the implant in the bone causes movement of the tibial implant under different loads. The legs with artificial knee joints were then fixed in the 4 point force assembly that is functionally similar to the assembly of FIG. 6, and subjected to a *varus* and valgus moment, respectively. CT scans were taken, and contours and three-dimensional data was generated. Following this the implant was fixed by adding bone cement and the measurement procedure was repeated. The three wedges with increments of 0.5 mm resulted in measured displacement increases of 0.50 mm, 0.55 mm and 0.42 mm, respectively. Furthermore, it was found that a threshold for the screw axis deviation could be determined at about 1.6°, which gave a positive result with a 95% confidence interval.

Example 3

A group of 6 patients that had been conventionally diagnosed with lose total knee arthroplasty were tested independently from the conventional assessment by the measurement of the laxity of the tibial component of the knee arthroplasty relative to the tibia by the method as described. Subsequently the patients were operated for revision of the total knee arthroplasty, and the looseness of the implants was evaluated by the operating surgeons. Table 2 depicts the values measured:

TABLE 2

| Patient No. | mTRE (mm) | Maximum Displacement (mm) | Result from operation |
| --- | --- | --- | --- |
| 1 | 1.00 | 1.00 | Lose |
| 2 | 0.41 | 0.37 | Fixed |
| 3 | 1.10 | 1.01 | Lose |
| 4 | 1.00 | 1.00 | Lose |
| 5 | 0.55 | 0.49 | Fixed |
| 6 | 0.81 | 0.79 | Lose |

The conclusion from the measurements was that four patients had a loose tibial component, whereas 2 had a tibial component that was not loose. With this data only, the positive and negative predicted value is 100%.

Summary of the Findings:

The present assembly, method and system are providing a possibility to avoid unnecessary surgical revision with an unprecedented ease, simplicity and accuracy.

The foregoing discussion discloses and describes merely exemplary arrangements of the present teachings. One skilled in the art will readily recognize from such discussion, and from the accompanying drawings, that various changes, modifications and variations can be made therein without departing from the spirit and scope of the present teachings.

The invention claimed is:

1. An assembly for a joint between a proximal segment of a limb that is proximal to the joint of the limb and a distal segment of the limb that is distal to the joint of the limb, the joint comprising a joint implant in a bone of the proximal segment and/or distal segment; and
    wherein the joint is being configured to allow rotation of the proximal segment and distal segment with respect to one another about an axis that intersects a first plane, wherein the first plane is the coronal plane, and to inhibit rotation of the proximal segment and distal segment with respect to one another about an axis that intersects a second plane and about an axis that intersects a third plane, both the second plane and the third plane being perpendicular to the first plane;
    the assembly being for subjecting the joint, at a predetermined angle of the joint rotation in the second plane and a predetermined angle of the joint rotation in the third plane, to a defined bending moment in the first plane, to induce a load to the joint implant that causes a movement of the joint implant in relation to at least one of: the bone of the proximal segment and the bone of the distal segment;
    the assembly comprising:
    (a) a proximal element configured for fixation of the proximal segment;
    (b) a distal element configured for fixation of the distal segment;
    (c) a linking element connecting the proximal element and the distal element, wherein the proximal element and the distal element each have a point fixed to each other via the linking element; and
    (d) a load application unit configured to:
    apply a desired load exposure to the proximal and distal elements to achieve the defined bending moment in the first plane of the assembly, wherein the defined bending moment is between the proximal and distal elements and the defined bending moment is in a direction perpendicular to an anatomic axis of the proximal segment of the limb or an anatomic axis of the distal segment of the limb.

2. The assembly according to claim 1 wherein the linking element rotatingly connects the proximal and distal elements to each other in the first plane or in a plane parallel to the first plane at a predetermined distance therefrom.

3. The assembly according to claim 1, wherein the load application unit comprises at least one surface to engage the joint from diametrically opposed directions.

4. The assembly according to according to claim 1, wherein the proximal and distal elements and the load application unit are arranged such that a uniform distribution of the defined bending moment is achieved along the joint or the proximal and distal elements are adapted to inhibit internal or external, or both, rotation between the proximal and distal elements about the axis of said first plane.

5. The assembly according to claim 1, wherein the proximal element, distal element, and load application unit consist essentially of materials transparent or essentially transparent to a radiation source.

6. The assembly according to claim 5, wherein the radiation source emits X-ray radiation, electrically non-conductive radiation, or both.

7. A method for a determination of a moment induced movement of a joint implant attached to a bone, in a joint between distal and proximal bones of an extremity, under a bending moment applied to the joint in a first plane defined by the direction of the moment, wherein the first plane is the coronal plane, the method comprising:
   (a) positioning the extremity in an assembly of claim 1 at a predetermined angle of joint motion in a manner allowing rotation of the joint about an axis that intersects the first plane, and inhibiting rotation of the joint in any plane perpendicular to the first plane;
   (b) exerting a predetermined amount of moment on the joint in a first direction in said first plane, and, using digital geometry processing, measuring position and orientation of the joint implant relative to the proximal or distal bone, or both, to obtain a first set of spatial position and orientation data;
   (c) exerting a predetermined amount of moment on the joint in a second direction opposing the first direction, and, using the digital geometry processing, measuring the position and orientation of the joint implant relative to the proximal or distal bone, or both, to obtain a second set of spatial position and orientation data; and
   (d) comparing said spatial position and orientation data as described in (b) and (c) to determine a movement of the joint implant relative to the bone to which it is attached;
wherein the bending moment is in a direction perpendicular to an anatomic axis of the proximal bone of the extremity or an anatomic axis of the distal bone of the extremity.

8. The method according to claim 7, wherein step (a) further comprises positioning the extremity in such fashion that the extremity is not subject to any external load and using the digital geometry processing, measuring the position and orientation of the joint implant relative to the proximal or distal bone, or both, to obtain the first set of spatial position and orientation data.

9. The method according to claim 7, wherein measuring of the spatial position and orientation data in step (b) or step (c) comprises generating a series of two-dimensional radiographic images taken along a single axis, by a CT- or MR scanner.

10. The method according to claim 7, further comprising
    (d) calculating a positional and orientational relationship between at least one component of the joint implant and the proximal and distal bones of the extremity based on the spatial position and orientation data from steps (b) and (c).

11. The method according to claim 7, wherein images are time-resolved images for generating data output of inducible movement of the joint implant over time, thereby allowing monitoring of progression of the inducible movement of the joint implant over time, and disease or change associated with a therapy, or allowing visualizations and associated calculated measurements associated with changes in the joint between the images taken at different time intervals.

12. A system for a determination of an induced movement of a joint implant under a bending moment using digital geometry processing, the system comprising:
    a) an assembly according to claim 1, and
    b) an apparatus configured and equipped for generating two-dimensional radiographic images taken along a single axis.

13. The system according to claim 12, wherein the apparatus is a CT scanner or MR scanner.

14. A method of preparing 3 dimensional images of a joint implant during a defined bending moment, the method comprising subjecting an assembly of claim 1 to scanning with a 3 dimensional scanning device while the assembly applies a desired load exposure to achieve the defined bending moment.

15. A kit of parts comprising:
    an assembly according to claim 1,
    an apparatus configured and equipped for generating two-dimensional radiographic images taken along a single axis, and
    a data processing device configured for, and operable for, comparing spatial position and orientation data from the two-dimensional radiographic images obtained with the apparatus to determine the movement of the joint implant in relation to the at least one of: the bone of the proximal segment and the bone of the distal segment.

16. The kit according to claim 15, wherein the apparatus is a CT scanner or MR scanner.

17. An assembly for a joint between a proximal segment of a limb that is proximal to the joint of the limb and a distal segment of the limb that is distal to the joint of the limb, the joint comprising a joint implant in a bone of the proximal segment or distal segment; and
    wherein the joint is being configured to allow rotation of the proximal segment and distal segment with respect to one another about a first axis, and to inhibit rotation of the proximal segment and distal segment with respect to one another about a second axis and a third axis, both the second axis and the third axis being perpendicular to the first axis, and the second axis is an anatomic axis of the proximal segment of the limb or an anatomic axis of the distal segment of the limb, and the third axis is the functional flexion extension axis;
    the assembly being for subjecting the joint, at a predetermined angle of the joint rotation about the second axis and a predetermined angle of the joint rotation about the third axis, to a defined bending moment about the first axis, to induce a load to the joint implant that causes a movement of the joint implant in relation to at least one of: the bone of the proximal segment and the bone of the distal segment;

the assembly comprising:
- (a) a proximal element configured for fixation of the proximal segment;
- (b) a distal element configured for fixation of the distal segment;
- (c) a linking element connecting the proximal element and the distal element, wherein the proximal element and the distal element each have a point fixed to each other via the linking element; and
- (d) a load application unit configured to apply a desired load exposure to the proximal and distal elements to achieve the defined bending moment about the first axis of the assembly, wherein the defined bending moment is between the proximal and distal elements and the defined bending moment is in a direction perpendicular to the anatomic axis of the proximal segment of the limb or the anatomic axis of the distal segment of the limb.

* * * * *